(12) United States Patent
Vanzin

(10) Patent No.: US 6,485,750 B2
(45) Date of Patent: *Nov. 26, 2002

(54) PHENOTHIAZINE IN PRILL FORM AND METHOD FOR MAKING THE SAME

(75) Inventor: David A. Vanzin, Franklin, TN (US)

(73) Assignee: Avecia, Inc., Wilmington, DE (US)

( * ) Notice: Subject to any disclaimer, the term of this patent is extended or adjusted under 35 U.S.C. 154(b) by 7 days.

This patent is subject to a terminal disclaimer.

(21) Appl. No.: 09/923,806

(22) Filed: Aug. 7, 2001

(65) Prior Publication Data

US 2002/0102310 A1 Aug. 1, 2002

Related U.S. Application Data

(63) Continuation of application No. 09/453,685, filed on Dec. 3, 1999, now Pat. No. 6,284,279.

(51) Int. Cl.$^7$ .......................... A61K 9/14; A61K 31/54; B29C 59/00; B01J 13/02
(52) U.S. Cl. ................ 424/489; 264/4.3; 264/115; 264/122; 424/489; 514/224.8; 514/225.2
(58) Field of Search ................... 424/451, 465, 424/489; 514/224.8, 225.2; 264/115, 117, 118, 122, 4.3

(56) References Cited

U.S. PATENT DOCUMENTS

| | | | |
|---|---|---|---|
| 3,912,727 A | * 10/1975 | Daniels | ........................ 260/243 |
| 3,951,638 A | 4/1976 | Bradley | |
| 3,975,472 A | 8/1976 | Packbier et al. | |
| 4,608,399 A | 8/1986 | Buysch et al. | |
| 4,897,436 A | 1/1990 | Buysch et al. | |
| 4,935,173 A | 6/1990 | Huey et al. | |
| 5,352,871 A | 10/1994 | Ross et al. | |
| 5,962,461 A | * 10/1999 | Anaebonam et al. | ....... 514/275 |
| 6,225,375 B1 | 5/2001 | Thibaut et al. | ............. 523/223 |
| 6,284,279 B1 | * 9/2001 | Vanzin | ........................ 424/489 |

FOREIGN PATENT DOCUMENTS

| | | | |
|---|---|---|---|
| DE | 1003137 A1 | * | 8/2001 |
| DE | 10032137 | | 8/2001 |

OTHER PUBLICATIONS

GMF Gouda, "Jet Priller".*
Zeneca Specialties, "PTZ Phenothiazine a Stabilizer for a Variety of Chemical Applications'"; Performance & Intermediate Chemicals; p. 1–10.*

* cited by examiner

Primary Examiner—Thurman K. Page
Assistant Examiner—S. Tran
(74) Attorney, Agent, or Firm—Law Offices of John A. Parrish

(57) ABSTRACT

Phenothiazine and its derivatives products are provided with a minimal level of fines or dust as a result of forming such products in prill form. The prills are generally spherical. Also provided is a method for reducing the level of powder in phenothiazine product which includes forming the phenothiazine product in prill form such that the prills have a generally spherical shape. The prill product achieves improved handling, flowability and dissolution times, while minimizing the generation of phenothiazine fines and dust, and the problems associated with worker exposure, irritation and sensitization to such fines and dust.

26 Claims, 1 Drawing Sheet

ND METHOD FOR MAKING THE SAME

PHENOTHIAZINE IN PRILL FORM AND METHOD FOR MAKING THE SAME

This application is a continuation of U.S. patent application USSN 09/453,685, filed Dec. 3, 1999, the priority to which is claimed, now U.S. Pat. No. 6,284,279.

BACKGROUND OF THE INVENTION

Phenothiazine is typically manufactured in flake form. Such flakes are formed by coating molten phenothiazine onto a drum flaker, where the product is cooled, and crystallizing the product to a solid which is flaked. The product is then conveyed to a physical separation process in which the product fines (powder) are separated from the flakes typically by the use of sizing screens. The product is then packaged and shipped to customers who convey or transfer the flakes through their own processing equipment. Despite product classification, the flakes tend to contain up to about 6% of product fines after manufacture. Further, the flakes are prone to further breakdown into fines during subsequent shipping and handling.

The generation of product fines or powder in the flake phenothiazine product presents problems. Flake products containing such fines suffer from the deficiencies of non-uniform particle size, caking, dustiness and clumping. Phenothiazine is a respiratory, skin, eye and gastrointestinal irritant and skin sensitizer, and is more likely to cause such problems when in the form of fines. Product fines in the flake product also increase the likelihood of product explosiveness. Flake product containing high levels of powder (i.e., greater than about 6% particles having a particle size of less than about 500 microns) is also prone to caking or clumping.

Non-uniform particle size in flaked product increases the tendency of the product to cake and/or clump and to resist ready flow transfer both internally and at customer facilities. The caking and/or clumping of the product makes it difficult to discharge from containers such as bins, bags, trucks, storage silos and the like and difficult to transfer. It may also have a tendency to bridge or block in containers. Product fines also present safety, health and environmental issues. From a safety standpoint, product fines are of particular concern due to the increased risk of explosion, as well as increased risk to employee health with respect to increased risk of skin irritation and skin sensitization and the like as noted above.

In accordance with the foregoing, there is a need in the art for a method to produce phenothiazine which reduces the problems associated with powder and fines in the finished product, but which still produces high quality phenothiazine. There is also a need in the art to reduce the problems associated with caking and/or clumping of phenothiazine product during shipment, transfer and storage.

BRIEF SUMMARY OF THE INVENTION

The invention includes a solid phenothiazine product, comprising a plurality of phenothiazine prills, wherein said prills are generally spherical.

The invention further includes a method of reducing the level of powder in phenothiazine product, comprising forming the phenothiazine product in prill form such that the prills have a generally spherical shape.

The invention also includes a solid phenothiazine product comprising a plurality of phenothiazine prills, wherein the prills are generally spherical and the product has no greater than about 6% by weight powder.

The invention includes a method for making phenothiazine in prill form, comprising introducing molten phenothiazine into at least one nozzle having a plurality of holes to form molten phenothiazine droplets; and cooling the droplets to form solid prills. The invention also includes a solid phenothiazine product formed by that method.

BRIEF DESCRIPTION OF THE SEVERAL VIEWS OF THE DRAWINGS

The foregoing summary, as well as the following detailed description of the preferred embodiments of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings, like numerals are used to indicate like elements throughout. In the drawings.

DETAILED DESCRIPTION OF THE INVENTION

Figure 1:
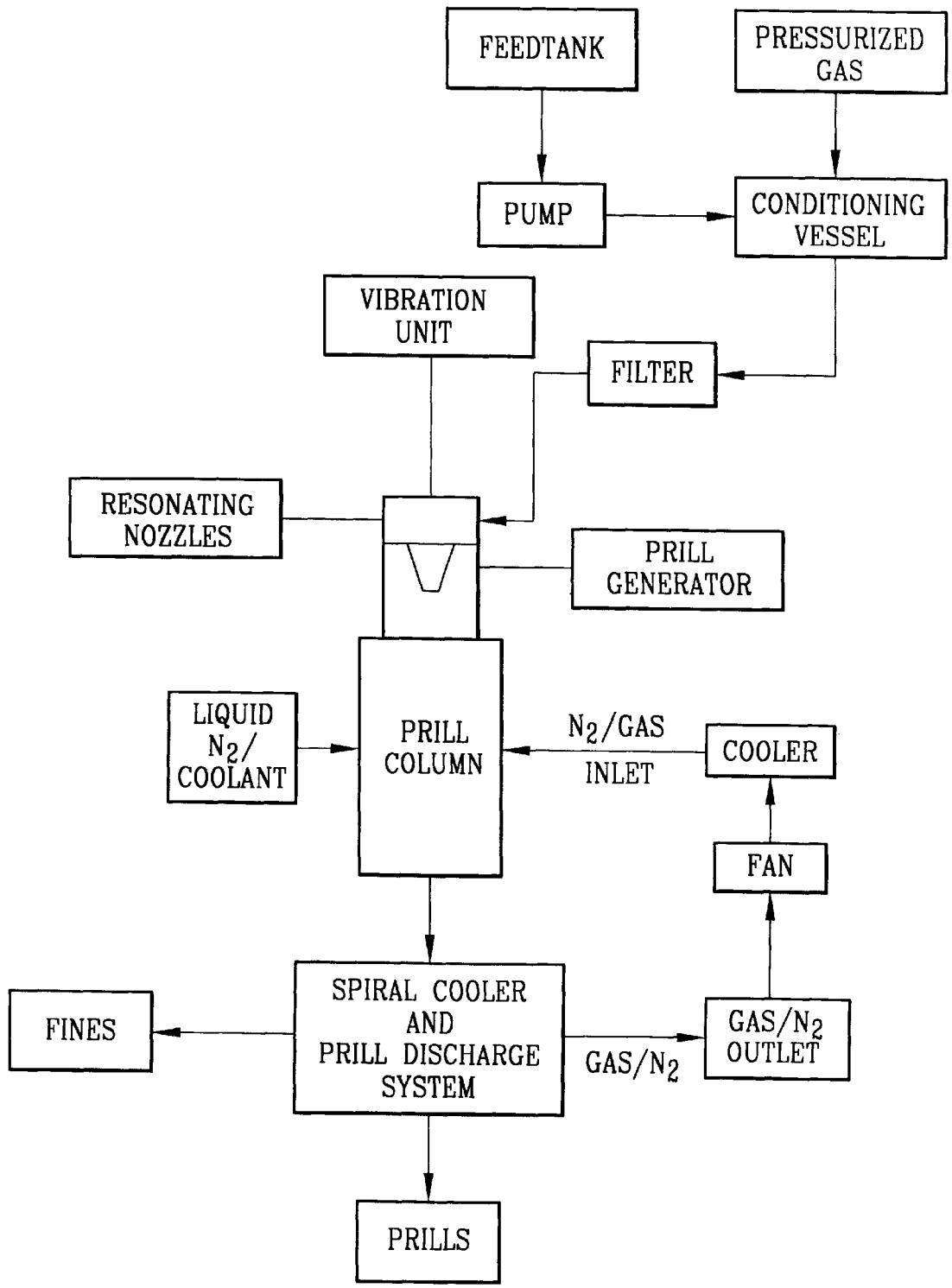
FIG. 1 is a schematic representation of a method for making phenothiazine prills in accordance with the invention.

The invention is directed to phenothiazine product having improved properties and reduced levels of fines, or powder, which is in prill form as well as to a method for making the phenothiazine product. The invention is further directed to a method for reducing the level of powder in phenothiazine product.

In accordance with the invention, a phenothiazine product is provided in prill form, wherein the prill form is generally spherical. The prills are formed by providing a molten phenothiazine feed into at least one nozzle having a plurality of holes to form molten phenothiazine droplets which are cooled to form prills. The feed material for forming the molten phenothiazine may be any available form of phenothiazine. Phenothiazine is a solid material which is currently commercially available in both flake and powder forms, however, other forms to be developed which could be formed into molten phenothiazine feed may also be used. As used herein, phenothiazine feed material may be any phenothiazine material, provided it is in solid form and can be made to be in a molten form, for example through application of heat. Phenothiazine for use as feed typically has a molecular weight of 199.26 and a chemical formula of $C_{12}H_9NS$. The commercially available phenothiazine typically has a melting point of 184° C. and a boiling point of 371° C. The bulk density is about 0.85 for flake product and about 0.75 for powder. The chemical formula is as follows:

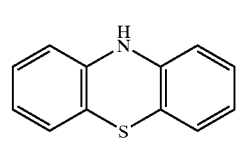

(I)

As used in this application, "phenothiazine" includes phenothiazine and its analogs and derivatives, including without limitation, compounds having formula (II) as shown below.

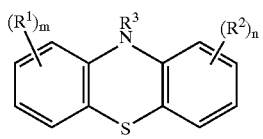

(II)

wherein $R^1$, $R^2$, and $R^3$ may be the same or different and may be hydrogen; halogens, such as chlorine and fluorine and the like; branched or straight chain, and substituted or unsubstituted hydrocarbon groups such as alkyl, alkenyl, or alkynyl groups of from 1 to 26 carbon atoms; substituted and unsubstituted aryl groups and aralkyl groups; or functional groups, including, but not limited to sulfonyl, carboxy, amine, alkylamine, hydroxy, carboxy, silyl, siloxy; and other similar derivatives and their salts. Substituted groups for hydrocarbon, aryl and aralkyl groups may include any of the above functional groups as well as elements such as oxygen, sulfur, silicon, nitrogen, and the like. Most preferably $R^1$, $R^2$ and $R^3$ in formula (II) are hydrogen. In formula (II), m and n are preferably independently from about 1 to about 4.

To form the prills, the phenothiazine feed in molten form, which may be phenothiazine in accordance with formulas (I) and/or (II) as well as phenothiazine derivatives, preferably those in accordance with formula (II), is fed into a jet priller capable of receiving a molten phenothiazine feed and passing the feed through nozzles having a plurality of holes. The basic method for forming the products of the invention is described with reference to FIG. 1.

The molten phenothiazine is preferably first melted at a temperature of preferably from about 205° C. to about 215° C. and under nitrogen pressure, then conditioned at a preferred temperature of about 200° C. at pressures of from about 1.5 to 3 bar when fed into the jet priller also under a nitrogen atmosphere. While these conditions are preferred for forming phenothiazine in accordance with formula (I), the conditions may be varied in accordance with the ordinary skill in the art to adjust for different, optimal melt temperatures for different grades of phenothiazine and for phenothiazine derivatives.

As the phenothiazine is fed to the priller head, it is preferably also first filtered to remove foreign material. As the feed passes through the holes, it is cooled to a solid, generally spherical, prill shape, preferably by very rapid chilling using liquid nitrogen and/or nitrogen gas. The use of nitrogen is important in order to maintain product quality and to achieve a yellow colored product. However, it should be understood, based on this disclosure, that other cooling gases, preferably other inert cooling gases, may be used to form phenothiazine prills according to the invention, however, a nitrogen gas is necessary for maintaining the preferred yellow color. Flow through the holes is controlled by pressure in the prill generator which is held substantially constant at between 0 and 1 bar. The feed is broken into droplets of from about 1 mm to about 2 mm by use of a resonance nozzle which is vibrated using a stroboscope at a frequency of from about 100 to about 1500 Hz, and preferably from about 400 to about 1100 Hz. The droplets then fall through a cryogenic freezing column where they are cooled immediately by liquid nitrogen into partially crystalline prills as they fall through the column. The column is also maintained under a cooled nitrogen atmosphere. The prills leaving the column are at approximately from about 120° C. to about 170° C., more preferably about 140° C., and pass into a spiral cooler which further cools and completes crystallization of the prills. In addition, the prills are separated from fines or dust along with nitrogen gas.

The separated nitrogen gas is chilled and is recycled to the cooling portion of the jet priller. The prill form product is removed from the jet priller and is useful for many applications, particularly those in which phenothiazine powder is problematic. FIG. 1 includes a flow diagram representation of the basic process for forming the phenothiazine prills using a jet priller as described above. A preferred jet priller is commercially available and/or prills can be manufactured using a jet priller from GMF Gouda, Goudsche Machinefabriek, B. V. in Waddinzveen, Holland, sold as Model JP15.

The phenothiazine prill product of the invention may be used in a wide variety of applications, including as a stabilizer for a variety of chemical applications. The product may also be used for an inhibitor, antioxidant and shortstopping agent in a variety of diverse applications such as the stabilization of acrylic acids, esters and monomers or as a stabilizer for chloroprene monomer/neoprene polymer, styrene monomer and other vinylic monomers. The prill product is also useful as an antioxidant in synthetic lubricants and oils, polyols for polyurethanes and polyester and vinyl ester resins. In addition, phenothiazine is a useful pharmaceutical intermediate. Due to its high level of activity, it functions at very low concentrations and enhances the functioning of other stabilizers. It will also function well in strongly acidic environments as well as in both air or nitrogen environments.

The prill products of the invention preferably have less than about 6% and more preferably less than about 1% by weight powder, wherein "powder" is a reference to product fines and/or powder particulates having particle sizes of less than about 500 microns. Further, the prills preferably have an average diameter as measured in the longest dimension of the prills of from about 0.5 mm to about 2.3 mm and more preferably from about 1 mm to about 2 mm. The generally spherical phenothiazine prills in accordance with the product formed in accordance with this invention have significantly improved flow characteristics due to the size uniformity and are safer to use than standard phenothiazine products in flake or powder form.

The invention will now be described in further detail with respect to the following non-limiting examples.

EXAMPLE 1

Experimental, small-scale simulation of phenothiazine prills was undertaken on a laboratory scale apparatus. A one liter, 3-neck reactor flask was used to simulate a flaker feed tank. It was equipped with nitrogen feed, a stirrer for agitation, a temperature probe and a bottom outlet. The apparatus was vacuum evacuated and nitrogen purged three times prior to product loading under nitrogen. The reactor was then charged, and the phenothiazine flake heated under nitrogen to a molten state at about 200° C. The molten phenothiazine was then slowly dripped through the bottom outlet valve (a simulated nozzle) into approximately one liter of liquid nitrogen (at about −192° C.) in a vacuum jacketed Dewar flask. Bright yellow prills were formed and subjected to selective analyses. The bright yellow prills met all product specifications, evidenced no precipitate, and handled in a manner and with an efficiency similar to standard phenothiazine flake product.

EXAMPLE 2

A larger scale trial was then undertaken. Phenothiazine product was charged to a holding vessel. The product was then melted at temperatures noted below, and conveyed under 3.1 bars pressure to a receiver vessel. The product was then fed into the prilling head of a Model JP15/1 Closed-Loop jet priller from GMF Gouda having 100 nozzles with a nozzle diameter of about 0.5 mm. The product flow was controlled by keeping the pressure in the jet priller head constant. In the prilling head, the product was broken into 1–2 mm droplets as passed through the nozzle. The nozzles contained between about 100 to 250 holes and flow through the nozzle was controlled by setting a vibrating membrane with the aid of a stroboscope at a frequency of 1005–1007 Hz. The product was forced through the holes and prills were formed. Prills were formed by immediate liquid nitrogen cooling of the molten droplet into a solid prill form. The molten feed was at approximately 200° C. (ranging generally from about 194.7 to 195.5° C.) and the liquid nitrogen temperature was about −192° C. The product solidified into a prill as it fell through the liquid/nitrogen gas environment in the cryogenic freezing column. Further cooling occurred on the spiral fluid bed, after which the product was discharged from the unit. Any generated product fines were removed by use of a cyclone. Nitrogen was recirculated back into the main unit after passing through a gas cooler. The trial resulted in the product of bright yellow prills which met all standard product specifications, evidenced no precipitate, and generated efficacy similar to standard phenothiazine flake product. The prills also offerred improved handling and flowability.

The prills as formed were generally spherical in shape and had an average diameter of about 1 mm. The prills also had a low angle of repose and exhibited a very narrow particle size distribution. Low powder levels of less than 1% were achieved, and the product was not prone to caking. The product also evidenced flow, transfer and handling characteristics equivalent to or superior to the existing flake product. Additionally, due to the more uniform shape and smaller average particle size, the prills demonstrated an enhanced dissolution time in comparison to flake product. A comparison of the properties of standard flake and the prills formed in this Example are shown below in Table 1.

TABLE 1

|  | Flake | Prill |
|---|---|---|
| Properties |  |  |
| Appearance | Yellow Flakes | Yellow Prills |
| Melting Point ° C. | 184 min. | 184.9 min. |
| Purity (%) | 99.6 | 99.9 |
| Angle of Repose | 36 | 25 |
| Bulk Density | 0.8 | 0.77 |
| Jar Shake Test for Powder | Slight to Heavy | Nil to Very Slight |
| Thickness (mm) | 1.40 | 1.65 |
| Average Diameter (mm) | N/A | 1 |
| Particle Size Distribution |  |  |
| ≧2360 microns | 75 | 0 |
| <2360 to 500 microns | 19 | 99 |
| <500 microns | 6 | 1 |
| Dissolution Time |  |  |
| Acetone (min.) | 5 | 3 |
| Methyl Methacrylate (min.) | 12.5 | 11 |
| Butyl Acrylate (min.) | 8 | 5.5 |
| Product Efficacy (hours to polymerize methyl methacrylate) | 13 | 14 |

Based on the foregoing, prills of phenothiazine were formed which attained properties which were at least comparable to those of standard phenothiazine products, and in most cases improved in comparison with standard phenothiazine products, and advantageously provided a substantially uniform average diameter and narrow particle size distribution as well as a very low level of fines. Such characteristics provided reduced incidences of caking and/or clumping and demonstrated improved flow properties in transport and in use. Other significant advantages obtained by using the prills include improvements to environmental and workplace safety as well as a reduction in the cost of manufacturing resulting from the low level of fines.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. A phenothiazine product, comprising a plurality of phenothiazine prills, wherein the prills are generally spherical and yellow.

2. The phenothiazine product of claim 1 wherein the prills have a melting point of 184.9° C. minimum.

3. The phenothiazine product of claim 2 wherein the prills have a purity of 99.9%.

4. The phenothiazine product of claim 3 wherein 99% by weight of the prills have a size between 500 microns to 2360 microns.

5. The phenothiazine product of claim 4 wherein less than 1% by weight of the prills have a particle size less than 500 microns.

6. A phenothiazine product, comprising a plurality of phenothiazine prills, wherein the prills are generally spherical, are yellow, have a melting point of 184.9° C. minimum, and the prills have a particle size distribution such that 99% of the prills have a size of from 500 microns to 2360 microns.

7. The phenothiazine product of claim 5 wherein the prills have a purity of 99.9%.

8. A phenothiazine product comprising a plurality of phenothiazine prills, wherein the prills are generally spherical, yellow, have a melting point of 184.9° C. minimum and a purity of 99.9% and a particle size distribution such that about 99% of the prills have a size of from 500 microns to about 2360 microns.

9. The phenothiazine product of claim 8 wherein less than 1% by weight of the prills have a particle size less than 500 microns.

10. A phenothiazine product comprising a plurality of phenothiazine prills, wherein the prills are generally spherical, are yellow, have a melting point of 184.9° C. minimum, less than 1% by weight of the prills have a particle size less than 500 microns, and the product has a angle of repose of 25.

11. A method for making phenothiazine in generally spherical prill form comprising:
    (a) introducing molten phenothiazine feed into a jet priller capable of receiving a molten phenothiazine feed and passing the feed through at least one nozzle which has a plurality of holes to form molten phenothiazine droplets; and
    (b) cooling the droplets to form solid phenothiazine prills.

12. The method of claim 11, wherein said molten phenothiazine is produced by melting phenothiazine at from about 205° C. to about 215° C. under nitrogen atmosphere.

13. The method of claim 12 wherein said molten phenothiazine is conditioned at about 200° C. at a pressure of from 1.5 to 3 bar; and introduced into said jet priller also under nitrogen atmosphere.

14. The method of claim 13, wherein said molten phenothiazine is filtered to remove foreign material.

15. The method of claim 11 wherein said droplets are cooled to a solid generally spherical, prill shape by an inert cooling gas.

16. The method of claim 15 wherein said droplets are cooled to a solid generally spherical, prill shape by liquid nitrogen and/or nitrogen gas.

17. A method for making a phenothiazine product in generally spherical prill form comprising:
   (a) charging phenothiazine product to a holding vessel;
   (b) melting said product;
   (c) conveying the molten product to a receiver vessel;
   (d) feeding said molten product into the prilling head of a jet priller and forcing the molten product through said holes;
   (e) controlling the flow through the nozzles by means of a vibrating membrane so as to form 1–2 mm droplets of molten product;
   (f) permitting said droplets to immediately fall through a cryogenic freezing column so as to form solid prills;
   (g) further cooling said prills; and
   (h) removing any generated fines.

18. The method of claim 17 where in step (c) the molten product is conveyed at about 200° C. and at a pressure of 3.1 bars.

19. The method of claim 18 where in step (d) said prilling head has 100 nozzles with a nozzle diameter of 0.5 mm, each nozzle having 100 to 250 holes.

20. The method of claim 19 where in step (e) said membrane is vibrating at a frequency of 1005–1007 Hz.

21. The method of claim 20 where in step (f) said cryogenic freezing column contains a coolant mixture comprising liquid nitrogen/nitrogen gas.

22. The method of claim 21 where in step (g) said further cooling is in a spiral fluid bed.

23. A method for making a phenothiazine product in generally spherical prill form comprising:
   (a) charging phenothiazine product to a holding vessel;
   (b) melting said product;
   (c) conveying the molten product at about 200° C. and a pressure of about 3.1 bars to a receiver vessel;
   (d) feeding said molten product into the prilling head of a jet priller having 100 nozzles with a nozzle diameter of 0.5 mm, each nozzle having 100 to 250 holes and forcing the molten product through said holes;
   (e) controlling the flow through the nozzles by means of a membrane vibrating at a frequency of 1005–1007 Hz so as to form 1–2 mm droplets of molten product;
   (f) permitting said droplets to immediately fall through a liquid nitrogen/nitrogen gas cryogenic freezing column so as to form solid prills;
   (g) cooling said prills further in a spiral fluid bed; and
   (h) removing any generated fines by means of a cyclone.

24. A method of making phenothiazine in prill form comprising:
   feeding molten phenothiazine into a nozzle which has a plurality of holes to form molten phenothiazine droplets, cooling the droplets with an inert gas or liquid to form solid yellow phenothiazine prills, and maintaining said prills in an inert nitrogen atmosphere.

25. The method of claim 24 wherein the inert gas or liquid is nitrogen.

26. The method of claim 24 which further comprises separating said prills from fines and dust.

* * * * *